United States Patent
Tschuncky et al.

(10) Patent No.: US 10,222,367 B2
(45) Date of Patent: Mar. 5, 2019

(54) CALIBRATING DEVICE FOR BREATH ALCOHOL MEASURING DEVICES

(71) Applicant: Dräger Safety AG & Co. KGaA, Lübeck (DE)

(72) Inventors: Peter Tschuncky, Lübeck (DE); Jochim Koch, Ratzeburg (DE); Stefan Morley, Lübeck (DE)

(73) Assignee: Dräger Safety AG & Co. KGaA, Lubeck (DE)

( * ) Notice: Subject to any disclaimer, the term of this patent is extended or adjusted under 35 U.S.C. 154(b) by 248 days.

(21) Appl. No.: 15/193,601

(22) Filed: Jun. 27, 2016

(65) Prior Publication Data
US 2016/0377597 A1     Dec. 29, 2016

(30) Foreign Application Priority Data

Jun. 29, 2015  (DE) .................. 10 2015 008 303

(51) Int. Cl.
*G01N 33/497*     (2006.01)
*G01N 33/00*      (2006.01)

(52) U.S. Cl.
CPC ..... *G01N 33/4972* (2013.01); *G01N 33/0006* (2013.01)

(58) Field of Classification Search
CPC ........... G01N 33/4972; G01N 33/0006; G01N 33/0008; G01N 27/4175; G01N 33/007; G01N 2033/0072
USPC .......... 73/1.03–1.07, 23.21, 23.3; 422/84, 85
See application file for complete search history.

(56) References Cited

U.S. PATENT DOCUMENTS

| | | | | |
|---|---|---|---|---|
| 4,474,048 A | * | 10/1984 | Schmidt | G01N 33/0006 436/9 |
| 4,521,038 A | * | 6/1985 | Cerny | A61M 16/08 128/202.27 |
| 5,929,319 A | * | 7/1999 | King | G01N 33/4972 422/84 |
| 6,526,802 B1 | | 3/2003 | Fisher et al. | |
| 7,422,723 B1 | * | 9/2008 | Betsill | G01N 33/4972 422/411 |
| 8,701,458 B2 | | 4/2014 | Emtell et al. | |
| 2002/0185081 A1 | * | 12/2002 | Schrader | A01K 31/04 119/479 |

(Continued)

FOREIGN PATENT DOCUMENTS

DE   195 45 794 C2   3/1998
DE   198 33 991 A1   2/2000

(Continued)

*Primary Examiner* — Robert R Raevis
(74) *Attorney, Agent, or Firm* — McGlew and Tuttle, P.C.

(57) ABSTRACT

A calibrating device (1) for a breath alcohol measuring device (25) as well as a system including such a calibrating device (1) and a breath alcohol measuring device (25) are shown and described. A test gas container (3), which provides a test gas, which can flow via an outlet (5) into an inlet (11) of a measuring adapter (9), is provided in the calibrating device (1). A measuring adapter (9) forms a flow path (17), in which the test gas is subjected to a dynamic pressure. The measuring adapter (9) is configured for being connected to a breath alcohol measuring device (25), which triggers a measurement when the dynamic pressure of the test gas reaches a pressure threshold value of the breath alcohol measuring device (25).

14 Claims, 1 Drawing Sheet

(56) References Cited

U.S. PATENT DOCUMENTS

2003/0167821 A1* 9/2003 Sussman ............ G01N 33/0006
73/1.06
2009/0056408 A1* 3/2009 Tryfonos ............... G05D 16/04
73/1.06
2010/0223975 A1 9/2010 Lueck et al.

FOREIGN PATENT DOCUMENTS

| DE | 103 16 333 B33 | 1/2004 |
| DE | 10 2004 049 064 B3 | 5/2006 |
| DE | 10 2010 022 745 B4 | 3/2012 |

\* cited by examiner

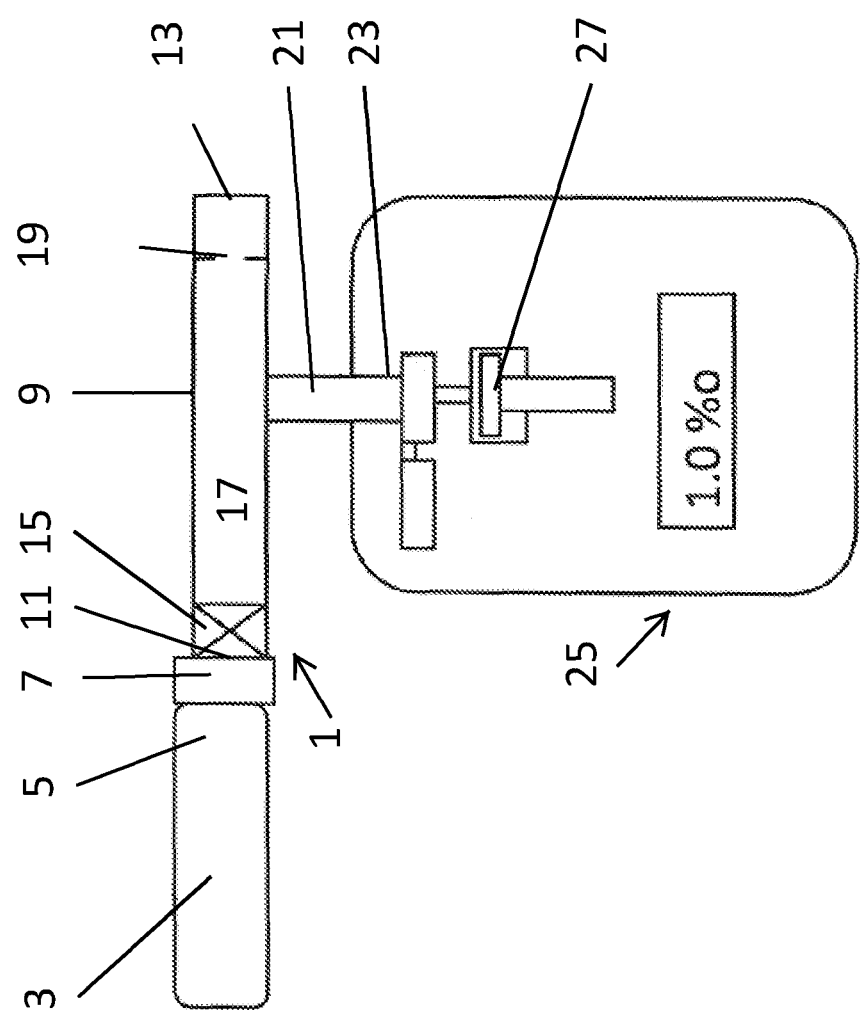

CALIBRATING DEVICE FOR BREATH ALCOHOL MEASURING DEVICES

CROSS REFERENCE TO RELATED APPLICATIONS

This application claims the benefit of priority under 35 U.S.C. § 119 of German Application 10 2015 008 303.1 filed Jun. 29, 2015 the entire contents of which are incorporated herein by reference.

FIELD OF THE INVENTION

The present invention pertains to a calibrating device for a breath alcohol measuring device as well as to a system comprising such a calibrating device and a breath alcohol measuring device.

BACKGROUND OF THE INVENTION

It is necessary in breath alcohol measuring devices to calibrate these at regular intervals in order to ensure that the displayed measured value corresponds to the actual alcohol level that is contained in the breathing air blown into the device.

It is sufficiently well known for this purpose that the devices in question are recalibrated by a correspondingly trained mechanic in a service facility, while the breath alcohol measuring device is exposed to a test gas that has a known alcohol content. Such a calibration performed by a service facility is extraordinarily expensive and therefore disadvantageous for the user.

Moreover, it is known from U.S. Pat. No. 6,526,802 B1 that a water-ethanol calibrating liquid is evaporated in a closed container, and this vapor is admitted to the breath alcohol measuring device in order to supply this with a gas having a defined alcohol concentration. However, the operation of such a device has also proved to be extraordinarily complicated.

SUMMARY OF THE INVENTION

Therefore, based on the state of the art, an object of the present invention is to provide a calibrating device, with which a breath alcohol measuring device can be calibrated in a simple manner.

According to a first aspect of the present invention, this object is accomplished by a calibrating device, with a test gas container, which provides a test gas under a pressure that is above the pressure of the atmosphere surrounding the calibrating device at an outlet; with a measuring adapter, which has an inlet and an outlet, wherein a flow path is formed between the inlet and the outlet, wherein the inlet is connected to the outlet of the test gas container, wherein the outlet is provided with a flow resistance, wherein the flow resistance is configured such that a dynamic pressure, which is above a preset value, builds up in the flow path in the test gas that flows from the outlet of the test gas container into the inlet and through the outlet, and wherein the measuring adapter has at the flow path a port for connection to a breathing gas inlet of a breath alcohol measuring device.

Accordingly, a test gas container with a pressurized test gas contained therein is provided in the calibrating device according to the present invention, wherein a measuring adapter, at the outlet of which a flow resistance is, in turn, provided, is provided in the calibrating device according to the present invention, so that when test gas is flowing from the test gas container through the measuring adapter, a dynamic pressure builds up in the latter. The test gas displaces air present in the measuring adapter through the outlet, so that this air does not contaminate the test gas and does not affect the alcohol content in the test gas. In addition, the flow path is provided with a port, at which the breathing gas inlet of a breath alcohol measuring device can be connected. When this happens and the breath alcohol measuring device is activated, it starts a measurement, because the dynamic pressure in the measuring adapter is selected to be such that its level corresponds at least to the threshold value at which the measuring device starts a measurement, or is higher than this threshold value.

It is ensured by such a configuration that a test gas with a defined alcohol concentration is admitted into the breath alcohol measuring device, and the conditions that must prevail during a real breath alcohol measurement of a test subject, i.e., a gas pressure with a predefined value in the breathing gas inlet of the measuring device, are simulated. In order for these conditions to be actually met, it is only necessary on the part of the manufacturer to correspondingly dimension the flow resistance, which may be configured, for example, as a diaphragm, and to provide test gas containers with a necessary pressure.

The use of a defined flow resistance makes it possible, on the one hand, for a predefined pressure to build up in the flow path at a predefined pressure in the test gas container, but, on the other hand, also to dispense with complicated devices, for example, a pressure reducer.

In a preferred embodiment of the calibrating device, a valve is provided in the measuring adapter between the inlet and the flow path, so that the connection between the measuring adapter or the flow path provided therein and the test gas container can be opened and closed by the user.

Moreover, it is preferred if a detachable adapter is provided at the inlet of the measuring adapter, so that the measuring adapter can be adapted to different outlets of different test gas containers.

Furthermore, it is preferred if the test gas is a carrier gas mixed with alcohol and it is especially preferably an ethyl alcohol-air mixture.

Furthermore, the above object is accomplished by a system with a breath alcohol measuring device and with an above-described calibrating device, wherein the flow resistance of the measuring adapter of the calibrating device is adapted such that the dynamic pressure building up in it is higher than the threshold value of the pressure at which the breath alcohol measuring device starts a measurement.

The present invention will be explained below on the basis of a drawing, which shows only a preferred exemplary embodiment.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view of an exemplary embodiment of a system comprising the calibrating device and a breath alcohol measuring device.

DESCRIPTION OF THE PREFERRED EMBODIMENTS

The exemplary embodiment of a system according to the present invention comprises a calibrating device 1, which has a test gas container 3, which is provided with an outlet 5 and in which an ethyl alcohol-water mixture is contained as a test gas. The test gas is under a pressure that is above the pressure of the atmosphere surrounding the system.

Via an adapter 7, which is detachably arranged at a measuring adapter 9, the outlet 5 of the test gas container 3 is connected to a measuring adapter 9. The measuring adapter 9 has an inlet 11 and an outlet 13. An actuatable valve 15 is provided at the inlet 11. The actuatable valve 15 connects the inlet 11 to a flow path 17, formed between the inlet 11 and the outlet 13. The actuatable valve 15 is configured to be opened by a user.

A flow resistance (throttle point) 19 in the form of a diaphragm is arranged at the outlet 13. A port 21 is arranged at the flow path 17. The system of the invention comprises the calibrating device 1 and a breath alcohol measuring device 25. The breath alcohol measuring device 25 of the system has a breathing gas inlet 23. The port 21 is connectable with the breathing gas inlet 23 of the breath alcohol measuring device 25 of the system.

The flow resistance 19 of the measuring adapter 9 is dimensioned such that a dynamic pressure, that corresponds to the pressure threshold value at which the breath alcohol measuring device 25 starts a measurement, builds up in the flow path when test gas flows from the outlet 5 through the adapter 7 and the valve 15 further through the flow path 17 from the outlet 13. A partial volume of a breathing gas, that is under a dynamic pressure, is usually removed for this from the flow path 17 by the stroke of a reciprocating pump 27 in the breath alcohol measuring device and fed to a suitable sensor.

To calibrate the breath alcohol measuring device 25, the calibrating device 1 is connected first, via the port 21 provided at the measuring adapter 9 of the calibrating device 1, to the breathing gas inlet 23 of the breath alcohol measuring device 25. The valve 15 is then opened, so that test gas will flow out of the outlet 13 through the flow path 17 and the flow resistance 19, and the aforementioned dynamic pressure will become established in the flow path 17. Since this pressure is selected to be such that this pressure is above the pressure threshold at which the breath alcohol measuring device 25 starts a measurement, such a measurement takes place when the device 25 is correspondingly activated. Since the test gas has a known alcohol concentration, such a measurement can be used to calibrate the device 25. The calibrating device 1 according to the present invention, comprising such a calibrating device 1, or the system according to the present invention, comprising such a calibrating device 1 and a breath alcohol measuring device 25, thus makes possible a simple calibration of the measuring device 25. Such a calibration can also be carried out by a user without major technical know-how.

While specific embodiments of the invention have been shown and described in detail to illustrate the application of the principles of the invention, it will be understood that the invention may be embodied otherwise without departing from such principles.

What is claimed is:

1. A calibrating device for calibrating a breath alcohol measuring device, the breath alcohol measuring device being configured to start measuring alcohol content in breathing gas blown into a breathing gas inlet by a test subject when a gas pressure of the breathing gas blown into the breathing gas inlet by the test subject exceeds the predefined pressure value, the calibrating device comprising:
   a test gas container providing a test gas that is under a pressure, that is higher than a pressure of the atmosphere surrounding the calibrating device, at a test gas container outlet;
   a measuring adapter with an adapter inlet and an adapter outlet, wherein a flow path is formed between the adapter inlet and the adapter outlet, the adapter inlet being connected to the test gas container outlet;
   a flow resistance provided with the adapter outlet, wherein the flow resistance is configured such that a dynamic pressure, which is above a predefined pressure value, builds up in the flow path in the test gas, which flows from the test gas container outlet into the adapter inlet and through the adapter outlet; and
   a measuring adapter port at the flow path configured to be selectively connectable to the breathing gas inlet of the breath alcohol measuring device.

2. A calibrating device in accordance with claim 1, further comprising a valve provided between the adapter inlet and the flow path, and configured for opening and closing the connection between the flow path and the test gas container outlet.

3. A calibrating device in accordance with claim 1, wherein the adapter inlet comprises a detachable adapter arranged between the adapter inlet and the test gas container outlet.

4. A calibrating device in accordance with claim 1, wherein the test gas is an alcohol in a carrier gas.

5. A calibrating device in accordance with claim 4, wherein the test gas is an ethyl alcohol-air mixture.

6. A calibrating device in accordance with claim 1, wherein:
   the preset threshold value is a condition that prevails during a real breath alcohol measurement of the test subject.

7. A calibrating device in accordance with claim 1, wherein:
   the breathing gas inlet of the breath alcohol measuring device is an inlet of the breath alcohol measuring device that is used during a real breath alcohol measurement of a test subject.

8. A system for breath alcohol measurement, the system comprising:
   a breath alcohol measuring device comprising a breathing gas inlet through which a test subject can blow breathing gas, wherein the measuring device is configured to start measuring alcohol content in the breathing gas blown into the breathing gas inlet by the test subject when a gas pressure of the breathing gas blown into the breathing gas inlet by the test subject exceeds a preset threshold value; and a calibrating device comprising:
a test gas container providing a test gas that is under a pressure, that is higher than a pressure of the atmosphere surrounding the calibrating device, at a test gas container outlet;
a measuring adapter with an adapter inlet and an adapter outlet, wherein a flow path is formed between the adapter inlet and the adapter outlet, the adapter inlet being connected to the test gas container outlet;
a flow resistance provided with the adapter outlet, wherein the flow resistance is configured such that a dynamic pressure, which is above a predefined pressure value, builds up in the flow path in the test gas, which flows from the test gas container outlet into the adapter inlet and through the adapter outlet; and
a measuring adapter port at the flow path configured to connect to the breathing gas inlet of a breath alcohol measuring device, wherein the dynamic pressure is selected to be such that the dynamic pressure is higher than the preset threshold value.

9. A system in accordance with claim 8, further comprising a valve provided between the adapter inlet and the flow path, and configured for opening and closing the connection between the flow path and the test gas container outlet.

10. A system in accordance with claim 8, wherein the adapter inlet comprises a detachable adapter arranged between the adapter inlet and the test gas container outlet.

11. A system in accordance with claim 8, wherein the test gas is an alcohol in a carrier gas.

12. A system in accordance with claim 11, wherein the test gas is an ethyl alcohol-air mixture.

13. A system in accordance with claim 8, wherein:
the measuring adapter port at the flow path is configured to be selectively connectable to the breathing gas inlet.

14. A system in accordance with claim 8, wherein:
the preset threshold value is a condition that prevails during a real breath alcohol measurement of the test subject.

* * * * *